United States Patent [19]

Frommer

[11] 4,422,761
[45] Dec. 27, 1983

[54] PHOTO-ELECTRIC PARTICLE SENSING SYSTEM

[76] Inventor: Joseph C. Frommer, 1525 Teakwood Ave., Cincinnati, Ohio 45224

[21] Appl. No.: 305,974

[22] Filed: Sep. 28, 1981

[51] Int. Cl.³ .............................................. G01N 21/47
[52] U.S. Cl. .................................... 356/338; 356/246; 356/342
[58] Field of Search ............... 356/336, 338, 339, 342, 356/244, 246, 317, 318; 250/573, 574, 576; 350/503, 504, 505, 294

[56] References Cited

U.S. PATENT DOCUMENTS

| | | | |
|---|---|---|---|
| 3,248,551 | 4/1966 | Frommer | 250/574 |
| 3,457,407 | 7/1969 | Goldberg | 356/338 X |
| 4,022,529 | 5/1977 | White | 356/318 |
| 4,088,407 | 5/1978 | Schoeffel et al. | 356/246 X |
| 4,188,543 | 2/1980 | Brunsting et al. | 356/339 X |
| 4,245,910 | 1/1981 | Källander | 356/338 |
| 4,311,387 | 1/1982 | deMey et al. | 356/318 |

Primary Examiner—William L. Sikes
Assistant Examiner—Matthew W. Koren
Attorney, Agent, or Firm—James W. Pearce; Roy F. Schaeperklaus

[57] ABSTRACT

A particle sensing system in which light is concentrated at an inspection zone and deflected light is concentrated at a photosensor. A first reflecting surface is shaped to direct light toward the inspection zone, and a second reflecting surface is shaped to direct light deflected by particles in the inspection zone toward the photosensor. These two reflecting surfaces can be shaped so that an overwhelming part of the directions around the inspection zone are utilized for illuminating it and to direct light deflected toward the photosensor. A third reflecting surface, having spherical curvature with the center of curvature at the inspection zone permits utilization of an overwhelming part of the remaining directions around the inspection zone.

19 Claims, 3 Drawing Figures

PHOTO-ELECTRIC PARTICLE SENSING SYSTEM

This invention relates to the photoelectric sensing of light deflected from its direction of propagation, such as occurs by the presence of microscopic or sub-microscopic particles in fluids, for the purpose of determining the number of particles present per unit volume and for obtaining information as to the size or size distribution of the particles and possibly other properties of the particles.

In systems for this purpose as in the systems described in U.S. Pat. No. 3,248,551 and 2,775,159, hydraulic or pneumatic means can be provided to cause a fluid to flow along a predetermined path, the "fluid path". Optical means are provided to concentrate illumination from a light source into a certain region, the "illuminated region" of this path. Further optical means are provided to cause as great a part as possible of the light deflected from its direction of propagation by particles in the fluid, to reach a photosensor. The region of the fluid path from which so deflected light reaches the photosensor, can be called the "observed region". The zone comprising the points which fall both into the illuminated region and the observed region can be called the "inspection zone". A centrally located point of the inspection zone can be called the "center of inspection". The portion of the inspection zone that is being illuminated and observed substantially identically with the center of inspection can be called the "inner inspection zone"; the rest of the inspection zone can be called the "outer inspection zone".

An object of the invention is to increase the illumination of the inner inspection zone as much as possible with the available light source, and to direct toward the photosensor as great a percentage as possible of the light deflected in the inner inspection zone without allowing light not deflected there to reach the photosensor.

Another object of the invention is to shape the inner and outer inspection zones so that particles transversing them on different paths cause as little statistical deviation as possible. The invention shall be explained by first discussing the illumination and observation of the center of inspection, which determines the illumination and the observation of the inner inspection zone.

The intensity of illumination of the center of inspection is a function of the solid angle under which the illumination from a light source of given brightness reaches it, i.e., of the solid angle under which the center of inspection "sees the light source". This solid angle may be visualized as the portion of a sphere imagined around the center of inspection, intersected by lines showing the directions from which the center of inspection is being illuminated. The area of this portion divided by the surface area of the entire sphere is a measure of how intensely a light source of given brightness illuminates the center of inspection, and can be called the "geometrical efficiency of illumination".

In the same way, the portion of the sphere intersected by lines showing the directions into which rays of light must be deflected to be directed toward the photosensor is a measure of how effectively the system "observes" the deflection of rays occurring in the inspection zone. The surface area of this portion of the sphere divided by the surface area of the entire sphere can be called the "geometrical efficiency of observation". Design of a system may be based on allocating directions of illumination and directions of observation on the sphere surrounding the center in inspection. This sphere can be called a "sphere of allocation". This invention shows ways in which a far greater part of the sphere of allocation can be utilized for illumination and for observation than was utilized in the art heretofore. It is based on the recognition of the fact that essentially all directions around the inspection zone can be utilized for either illumination or observation if only no direction of illumination continued beyond the inspection zone coincides with a direction of observation. To divide all directions around the inspection zone into directions of illumination and of observation, the geometrical fact can be used that all rays reaching the apex of a cone from inside the cone continue beyond the apex inside the cone, and all rays reaching the apex from outside the cone continue beyond the apex outside the cone.

Briefly, this invention provides a system for sensing light deflected by particles in a fluid in which the fluid is directed along a fluid path through an inspection zone. A first optical means concentrates light from a light source into the inspection zone. A second optical means directs light deflected by particles at the inspection zone toward a photosensor. Each one of these two optical means comprises a light reflecting surface which faces the inspection zone. One of the light reflecting surfaces is located outside an imagined "partitioning cone", which partitions the directions around the inspection zone into directions of illumination and directions of observation. The other of the light reflecting surfaces is located inside that partitioning cone.

The drawings illustrating the invention are FIGS. 1 to 3, of which:

Figure 1:
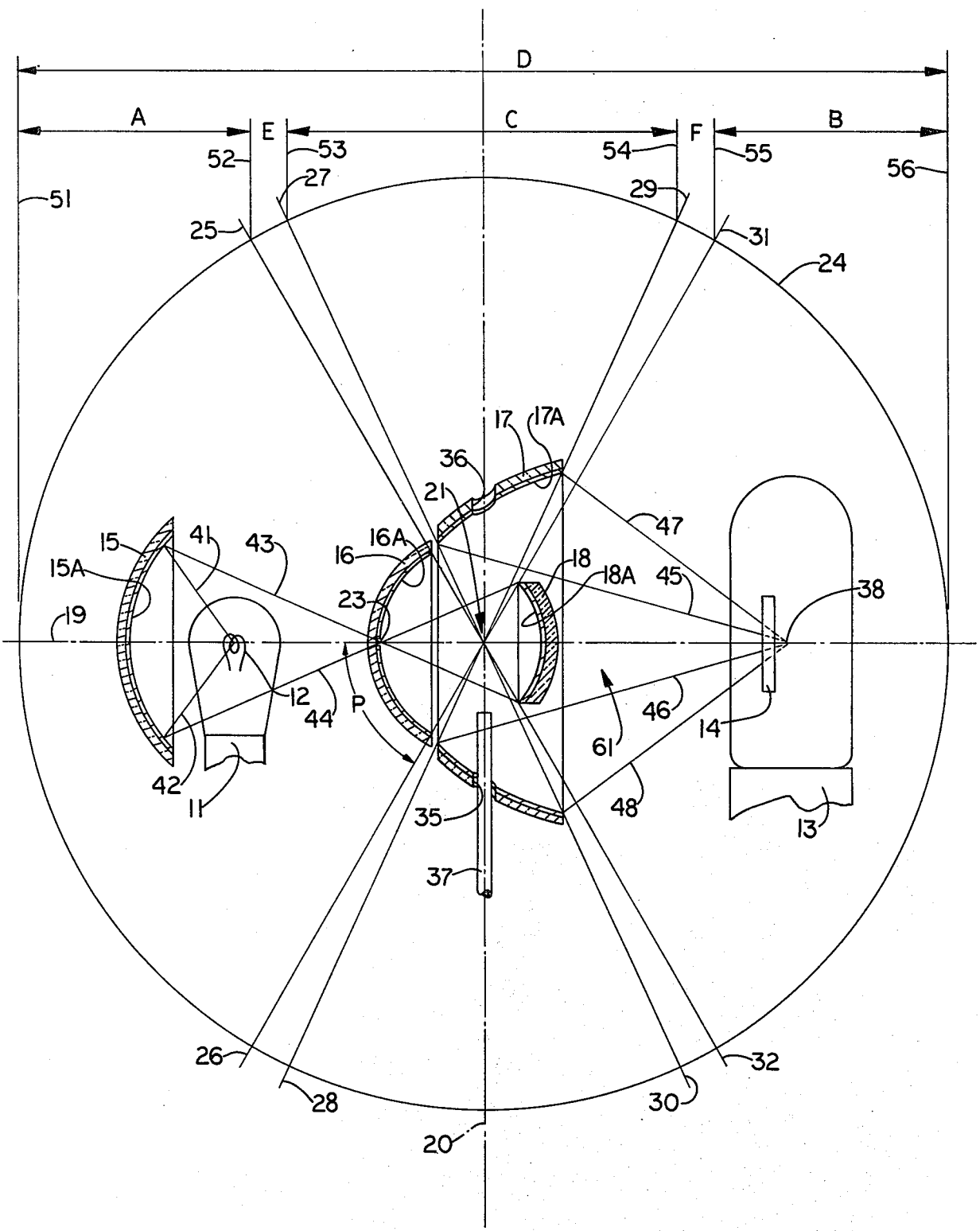
FIG. 1 is a schematic cross-sectional view of an optical system illuminating and observing dust particles in air, which is constructed in accordance with an embodiment of this invention.

In the drawings, embodiments of the invention are shown in cross section. In drawings 1 and 3, a sphere of allocation and half cones that enclose directions in which the center of inspection is being illuminated and observed are shown by their intersections with the plane of the drawing.

In FIG. 1, a dot-dash line 19 represents the optical axis of the system. A point 21 on the line 19 is the center of inspection. Air to be tested is sent by a nozzle 37 through a window or hole 35 in a stream along a dash-dot line 20, which intersects the optical axis 19 perpendicularly at the center of inspection 21. The air can exit through a second window or hole 36. An incandescent lamp 11 has its filament 12 located on the optical axis 19. A photosensor 13, e.g., a photo-multiplier tube, has its light sensitive surface or photocathode 14 centered around the optical axis 19. Front surface mirrors are indicated at 15, 16, 17 and 18 with reflecting surfaces 15A, 16A, 17A and 18A. Mirrors 15, 16 and 18 are substantially saucer shaped; the mirror 17 is annular. The curvature of mirror 15 is elliptical, i.e., it has the property of a segment of an ellipsoid (obtained by rotating an ellipse around its major axis) to reflect rays from the vicinity of one of its focal points toward the vicinity of the other of its focal points. The reflecting surface 15A is a section of an ellipsoid generated by the rotation of an ellipse around the optical axis 19. One focus of this ellipse is at the filament 12, and the other focus is at a transparent opening or light concentration zone 23 in the reflecting surface 16A of the mirror 16 at its intersection with the optical axis 19. The mirror 15 reflects rays, such as the rays 41,42 into rays such as 43,44, which proceed through the transparent opening 23 toward the mirror 18. Practically, small deviations from the exact shape of an ellipsoid are tolerable. In certain applications, a spherical shape, which is easier to produce, may also be used, because a sphere not only reflects rays from the close vicinity of its center of curvature back to the close vicinity of its center of curvature, but it also conjugates points at one side of its center of curvature with points on the opposite side of its center of curvature. The mirror 18 is also elliptical and is saucer-shaped. It has one focus at the transparent opening 23 and another focus at the center of inspection 21. The rays 43,44 are drawn to the border of the reflecting surface of the mirror 18. The direction of their reflection is shown by lines 32,31, respectively, which are extended to a sphere of allocation 24. The curvature of the elliptical mirror 18 is far more critical than that of the mirror 15, since it determines how the image of the opening 23 appears at the inspection zone. In the absence of particles in the inspected fluid, the rays traversing the center of inspection 21 proceed undeflected toward the mirror 16. This mirror 16 is spherical and has its center of curvature at the center of inspection 21. The mirror 16 reflects these rays back in the same direction. Therefore, illumination is provided from both the mirror 18 and the mirror 16 over solid angles determined by half cones imagined from the center of inspection to the border of the mirror 18, as defined by rotation of the ray lines 31,32, and to the border of the mirror 16 shown by the lines 25,26. For mirror 16 to reflect back all rays thrown onto the center of inspection by mirror 18, these two half cones must be the two halves of one and the same full cone; lines 31,32 must be straight continuations of lines 26,25.

If a particle appears at the center of inspection 21, some rays reaching it will be deflected. Available to signal the presence of such a particle are the rays that are deflected neither toward the mirror 16 nor toward the mirror 18. The annular mirror 17 is provided to direct these rays toward the photosensor 13. This mirror 17 is elliptical and has one focus at the center of inspection 21 and another focus at a point 38 situated on the optical axis 19 behind the photocathode 14, which is at a second light concentration zone. The annular elliptical mirror 17 reflects rays between the lines 27,29 and 28,30 into rays between lines 45,47 and between lines 46,48. The line 29 is a straight continuation of the line 28; the line 30 is a straight continuation of the line 27. The half cones 27,38 and 29,30 are the two halves of one and the same full cone.

A free space 61 is formed inside the cones defined by ray lines 45,46 and ray lines 29,30, which is not traversed by rays deflected to the annular elliptical mirror 17 and reflected by it toward the photocathode 14. The saucer-shaped elliptical mirror 18 is mounted in the free space 61 with one of its foci at the center of inspection, as already indicated. The annular elliptical mirror 17 is located outside a full cone defined by the ray lines 27,28 and 29,30, and the saucer-shaped elliptical mirror 18 is located inside the half cone defined by the ray lines 31,32. The annular mirror 17 has the shape of a segment of an ellipsoid limited by two planes perpendicular to its major axis and the saucer-shaped mirror 18 has the shape of a segment of another ellipsoid limited by a single plane perpendicular to its major axis.

The directions around the center of inspection allocated to illumination and to observation in this embodiment of the invention can be visualized on the surface of the sphere of allocation 24. All directions of illumination intersect the sphere of allocation 24 left of a line 52 (for illumination from the mirror 18), and to the right of a line 55 (for illumination from the mirror 16). The directions of observation intersect the sphere 24 between lines 53 and 54 in an annular shape. The surface areas of these segments are such fractions of the surface area of the entire sphere as are the lengths of their projections onto the optical axis to the diameter of the sphere. If we call the lengths of these projections A, B, and C, and the diameter of the sphere (between the lines 51 and 56) D, the geometrical efficiencies of illumination and of observation are $A/D+B/D$ and $C/D$. The portions of the sphere of allocation not used for either illumination or observation are the two segments between the lines 52,53 and between the lines 54,55. If we call the widths of these two unused segments E and F, as shown by the so marked dimension lines, we can say that the sum of the geometrical efficiencies of illumination and of observation falls short of the theoretical maximum of one by $E/D+F/D$. This loss of efficiency is necessary to prevent light reaching the inspection zone outside the center of inspection from getting directed toward the photosensor. The margin between the directions in which the mirrors 17 and 18 face the center of inspection is necessary because the rays that reach the peripheral points of mirror 18 from peripheral points of the opening 23 could otherwise reach peripheral points of the mirror 17. The size of the opening 23 (which determines the size of the illuminated region around the center of inspection) and the distance between the opening 23 and the mirror 18 determine the margin necessary between the cones limiting the mirrors 17 and 18. The closer the mirrors 17 and 18 are to an inspection zone of a given size, the larger is the necessary margin that must be left between the angles of the cone 27,28, 29,30 and the cone 25,26, 31,32. The necessary margin can be determined on the drawing board by ray tracing. Design may start with extending the reflecting surfaces 16, 17 and 18 to a partitioning cone such as the cone 25,26, 31,32 without any margin and programming a computer to tell the margin necessary between this partitioning cone and the cone 27, 28, 29, 30 outside it to avoid rays leaving the mirrors 16 and 18 which are not deflected by particles, from reaching the mirror 17. But the necessary margin may be determined also empirically by building pilot units with insufficient margin and masking their periphery with black paint or black tape as far as necessary to bring DC output of the photosensor to an acceptable level. Alternatively, the departure may be with a partitioning cone 27,28,29,30 and finding the necessary margin between it and the cone 25,26,31,32. In principle, design could also start with providing equal margins between a partitioning cone and the cone 25,26,31,32 inside it and the cone 27,28,29,30 outside of it.

Regarding the angle of the partitioning cone, any angle P around 60 degrees between the optical axis 19 and the partitioning cone 25,26,31,32 carves out about equal surface areas inside the partitioning cone and outside it from the sphere of allocation 24. This holds the product of the geometrical efficiencies of illumination and of observation close to its possible maximum.

But the fact that different size particles deflect light in very different patterns and other design considerations may sway the choice farther away from 60 degrees.

In FIG. 1, the mirrors 16 and 17 are shown as separate mirrors but can be incorporated in a single unitary piece.

Figure 2:
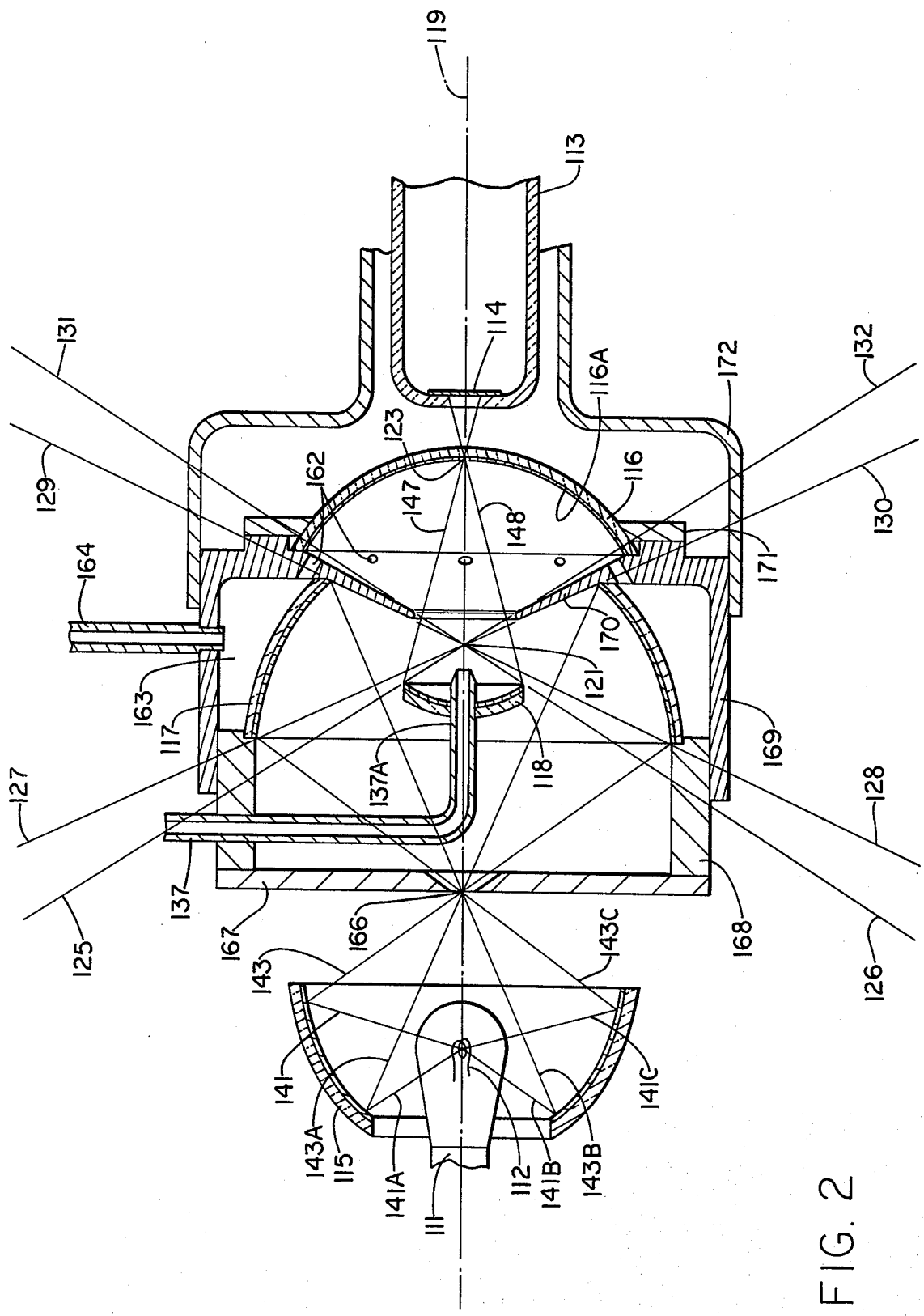
FIG. 2 is a schematic cross-sectional view of another system for inspecting dust in air.

FIG. 2 shows the cross section of another dust particle counter according to the invention, using a similar principle of illuminating and observing as FIG. 1, but in which an annular mirror 117 provides the illumination and two saucer-shaped mirrors 118 (elliptical) and 116 (spherical) direct the light deflected by particles in an inspection zone 121 toward a photosensor 113. A photocathode 114 of the photosensor 113 is circular and is placed behind a transparent opening 123 in a reflecting surface 116A of the mirror 116. A sampled air stream is blown through a nozzle 137A of a tube 137 toward the center of inspection 121 in a stream centered along an optical axis 119, so that particles traverse the inspection zone in directions parallel to the optical axis 119. The air escapes through holes 162 into a compartment 163 from which it is removed by a tube 164. The air stream blown toward the inspection zone is centered around the optical axis 119 for the following reason: The signal generated by a particle traversing the inspection zone depends on the size and the shape of the particle, but also on what path it takes inside the inspection zone. If the particles traverse an inspection zone that is illuminated and observed by a central-symmetrical optical system in the direction of the optical axis of this system, then signals obtained by identical particles proceeding on various paths will deviate less from each other.

A filament 112 of a lamp 111 is focused by a mirror 115 onto an opening 166 of a wall 167. The mirror 115 is annular, to illuminate the annular mirror 117. Rays 141, 141A, 141B and 141C from the filament 112 are reflected by the mirror 115 as rays 143, 143A, 143B and 143C, respectively. The foci of the mirror 117 are at the hole 166 and at the center of inspection 121.

The spherical mirror 116 has its center of curvature at the center of inspection 121. The mirror 116 reflects rays deflected toward it by particles in the inspection zone back toward the inspection zone and hence to the mirror 118. The mirror 118 is elliptical, and has its focal points at the center of inspection 121 and at a transparent opening 123 in a reflecting coating 116A of the mirror 116. Rays deflected by particles in the inspection zone 121 are reflected by the mirror 118 and by the mirror 116. The mirror 116 reflects such deflected rays back through the inspection zone 121 to the mirror 118. The deflected light is reflected by the mirror 118 along ray lines 147–148 into the opening 123 to reach the photocathode 114 of the photosensor 113. This round cathode 114 is held at such a distance from the opening 123, that practically its entire surface is utilized.

Cylinder 168 seats the mirror 117; 169 is a cylindrical body fitted over the cyliner 168, having a seat for the mirror 116 and a conical extension 170 to shield the opening 123 from stray light. A flat ring 171 holds the mirror 116 at its seat. A cover 172 connects to a socket of the photomultiplier 113 (not shown) and completes the exclusion of outside light.

Lines 125 through 132 show the directions in which half cones extended to a sphere of allocation (not shown, but similar to that shown in FIG. 1) would intersect that sphere. Lines 125, 126 show the directions of the limiting rays toward the mirror 118, lines 127, 128, 129, 130 show these for the mirror 117, and lines 131, 132 show these for the limiting rays that reach the mirror 116.

The directions of illumination are outside of the two half cones obtained by rotating lines 127,128 and 129,130 around the optical axis 119, and the directions of observation are inside the two half cones obtained by rotating the lines 125,126 and 131,132 around the optical axis 119. The half cones 125,126 and 131,132 must be located wholly inside and the half cones 127,128 and 129,130 must be located wholly outside a common partitioning cone.

Figure 3:
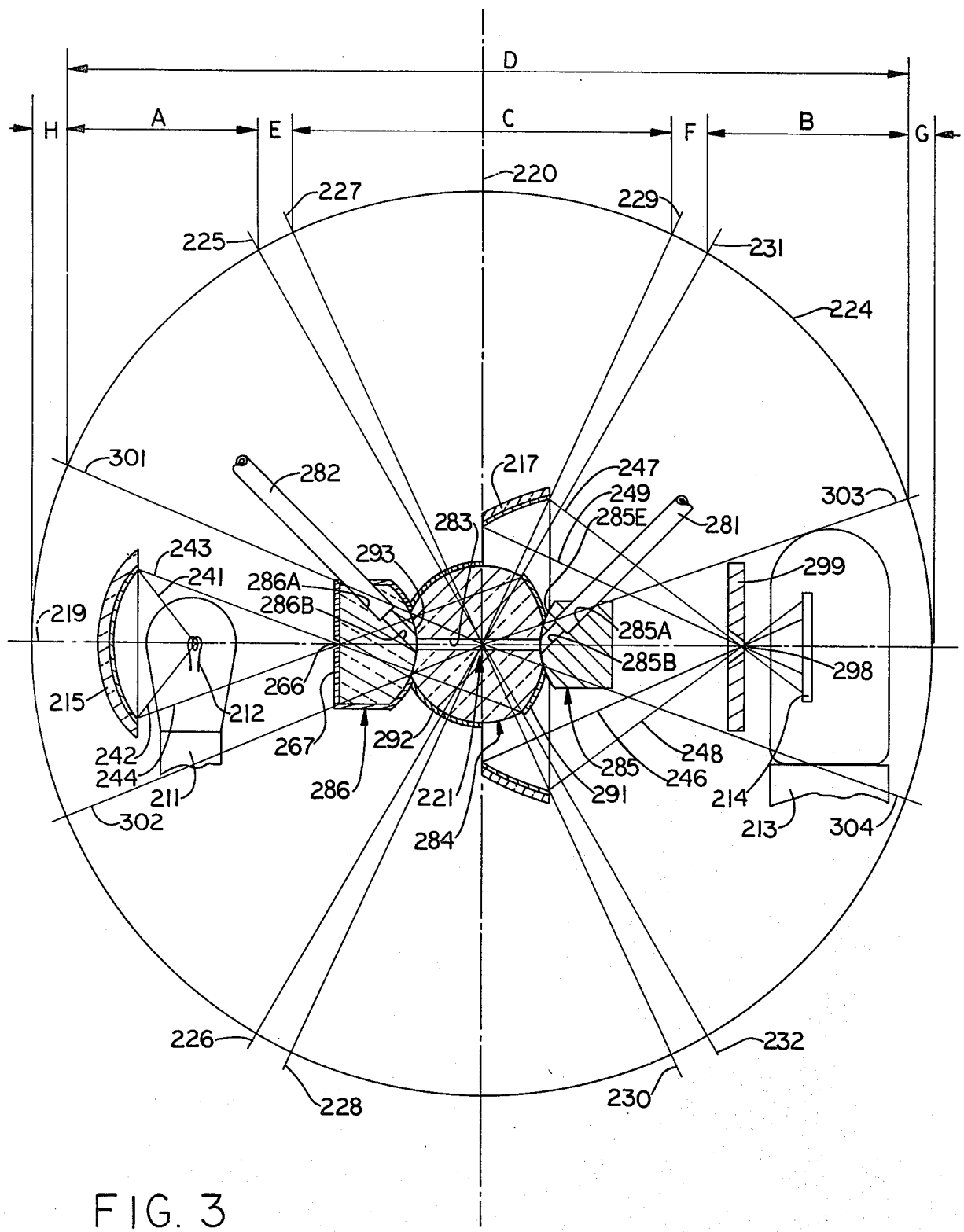
FIG. 3 is a schematic cross-sectional view of a system for detecting particles in a liquid.

FIG. 3 shows the cross section of a system for testing a fluid, e.g., a solution of blood for its content of blood cells. In this figure, line 219 is the optical axis and point 221 on the line 219 is the center of inspection. A ball-shaped transparent body 284 is optically ground and covered with reflecting coatings 291, 292. The fluid to be inspected is introduced and discharged by opaque tubes 281, 282 to and from an inspection bore 283 centered around the optical axis 219. Hermetic sealing between these two tubes and the body 284 is provided by end pieces 285, 286. The end piece 285 is opaque. It is cylindrical with its axis at the optical axis 219. One of its ends is flat; an opposite end 285E is spherical. It is provided with a hole 285A to accommodate the tube 281 and a hole 285B to conduct the fluid between the tube 281 and an inspection bore 283. The end piece 286 is also cylindrical with its axis at the optical axis 219, with one end flat and an opposite end 293 spherical. It is transparent and covered with an opaque coating 267. This coating extends over the whole cylindrical surface, the spherical portion outside a cone 301, 302 and the flat portion excepting a transparent opening 266. The end piece 286 is provided with bores 286A and 286B to accommodate the tube 282 and to transmit the fluid between this tube and the inspection bore 283. The walls of the bores 286A and 286B are opaque.

The shape of the body 284 is limited by a sphere having its center of curvature at the center of inspection 221. Between half cones 231,232 and 303,304, the face of the body 284 is ground elliptically for focal points at the center of inspection 221 and the transparent opening 266. Inside the half cone 303,304, it is ground spherically to match the end piece 285. Inside half cone 301,302 it is ground spherically to match the end piece 286. It is covered with the reflecting coating 291 on the elliptical portion between the half cones 231,232 and 303,304 and with the reflecting coating 292 between the half cone 301,302 and a plane erected perpendicularly at the line 220 which intersects the optical axis 219 perpendicularly at the center of inspection 221.

An elliptical mirror 215 has one focus at a filament 212 of a lamp 211 and another focus at the opening 266 to reflect light between rays 241,242, as indicated by rays 243,244 toward the transparent opening 266. These rays reach the reflecting surface 291 through the spherical portion 293 of the end piece 286 and are reflected between the directions indicated by extended ray lines 232,231 toward the center of inspection 221. Most of these rays reach the reflecting surface 292 between the half cone 225, 226 and the half cone 301,302 which limits the reflecting coating. The reflecting coating 292 reflects these rays back toward the center of inspection from the opposite side. Thus, illumination of the center of inspection occurs in directions inside the two half cones obtained by rotating the lines 231,232 and lines 225,226 around the optical axis 219.

Rays deflected into directions between the lines 229 and 230 drawn to the right side edge of the annular mirror 217 and the plane indicated by the line 220 at the left side edge of the annular mirror 217 reach the annular mirror 217 directly. Rays deflected in the directions between the plane 220 and a half cone indicated by ray lines 227,228 drawn as the straight continuation of lines 230,229 reach the annular mirror 217 after reflection by the spherical reflecting surface 292 back toward the inspection zone and from there to the mirror 217. The annular mirror 217 has one focus at the center of inspection 221 and anothr focus at an opening 298 in a baffle 299. The light sensitive surface 214 of the photomultiplier 213 is located behind the transparent opening 298 of the opaque panel 299 in such a way that the light reflected by the mirror 217 reaches as much of its surface as possible. In this way, rays deflected in the inspection zone in directions outside the full cone 227, 228, 229, 230 are reflected by the mirror 217 toward the transparent opening 298 as indicated by ray lines 246,247,248,249, and hence to the photocathode 214.

All directions outside the half cones 227,228 and 229,230 are directions of observation, and directions inside half cones 224,226 and 231,232 are directions of illumination. Lost are only the directions between the half cones 227,228 and 225,226 on one side, between the half cones 229,230 and 231,232 on the opposite side, as well as the rays inside the half cones 301,302 and 303,304. These losses are shown as the widths of the segments that the respective cones cut out of the sphere of allocation 224 and marked E, F, G, H by the same reasoning as was presented in connection with FIG. 1. Illuminating rays lost at the opaque bore 286B and deflected rays lost at the opaque tube 281 could be accounted for by corresponding spots on the sphere of allocation 224. The width of two annular segments of the sphere of allocation 224 equal in surface area to the surface area of these two spots would be so small that they would not show if they were drawn to scale to diminish the widths of the segments A, B, C showing the solid angles available for illumination and observation.

The mirror geometry shown in FIG. 3 can be employed for dust particle counting by use of three separate mirrors for the mirror 217 and for the reflecting surfaces 291 and 292 in a way as provided in FIG. 1. Alternately, a unitary piece could be used for the function of the mirror 217 and the reflecting surface 292 after bringing the left edge of the mirror 217 and the right edge of the reflecting surface 292 closer to each other.

The drawings show the essence of the invention as simply as possible. Enclosures to keep out outside light and light traps to prevent stray light from reaching the photocathode are shown only on FIG. 2.

According to the invention, illumination and observation is provided by dividing all directions around the center of inspection into essentially two parts: inside and outside a full cone, the "partitioning cone" having its apex at the center of inspection. All directions of observation are kept inside this cone and all directions of illumination are kept outside this cone, or vice versa. Lines 25 through 32 of FIG. 1, lines 125 through 132 of FIG. 2 and lines 225 through 232 of FIG. 3 show the margin between the directions of illumination and observation discussed in connection with FIG. 1.

In the preferred embodiments of the invention shown in the figures, an annular elliptical reflecting surface faces the center of inspection on the outside of the partitioning cone, and a saucer-shaped elliptical reflecting surface faces the inspection center at the inside of the partitioning cone. A spherical reflecting surface faces the center of inspection from almost all directions from which it is not faced by the said annular or the said saucer-shaped mirror. The spherical reflecting surface can be provided with a transparent opening through which the saucer-shaped elliptical mirror receives or sends light rays according to whether the saucer-shaped elliptical mirror illuminates the inspection zone or directs deflected rays of light toward the photosensor.

In the preferred embodiments shown, the annular elliptical mirror facing the inspection zone from the outside of the partitioning cone must be kept large enough so that the rays reflected by it clear the saucer-shaped reflecting surface on their way toward the photosensor or from the light source. The physical size of the annular elliptical mirror can be reduced by replacing the part of it that would fall on one side of a plane erected at the center of inspection by the spherical reflecting surface having its center of curvature at the center of inspection, so that the spherical reflecting surface reflects rays reaching it from the inspection zone both toward the saucer-shaped and the annular reflecting surface on the opposite side of this plane. In the preferred embodiment shown in FIG. 3, this plane is perpendicular to the axis of the partitioning cone, but it would perform the same function if it was selected at any other angle as long as it stayed outside the partitioning cone.

Each of the elliptical mirrors can be of true ellipsoidal shape and can have two spaced foci or can be a reflecting surface departing slightly from a perfect ellipsoid shape whether the departure is caused for ease of manufacture, by technical imperfection or is purposefully provided to make various points of the inspection zone more uniform regarding geometrical efficiency. Each elliptical mirror must conjugate two focal zones so that a majority of the light rays reaching the reflecting surface from one focal zone is reflected into the other focal zone, but neither elliptical mirror requires perfect conjugation of two focal points.

The optical axes of the annular and saucer-shaped reflecting surfaces are preferably identical with the axis of the cone of partition.

The fluid to be tested can be caused to flow in a stream centered along the optical axis of the system.

The particle sensing systems illustrated in the drawings and described above are subject to structural modification without departing from the spirit and scope of the appended claims.

Having described my invention, what I claim as new and desire to secure by Letters Patent is:

1. A photoelectric system for sensing light deflected from its direction of propagation by small particles in a fluid comprising a source of light, a photosensor having a light sensitive surface, two spaced light concentration zones and an inspection zone, means for directing the fluid to the inspection zone, a first of the said light concentration zones receiving light from the source of light, the said inspection zone being created by providing a first light concentrating reflecting surface so designed and arranged that it concentrates light from said first of the light concentration zones into the inspection zone and a second light concentrating reflecting surface so designed and arranged that it concentrates light deflected by particles at the inspection zone from the inspection zone toward a second of the light concentration zones, the said light sensitive surface being so placed that it intercepts light concentrated by the said second light concentrating reflecting surface toward the second of the light concentration zones, one of the said reflecting surfaces being located wholly outside a full cone having its apex at the inspection zone and the other of the said reflecting surfaces being located wholly inside the said full cone, the first light concentrating reflecting surface being of annular shape, whereby the space traversed by rays that the annular reflecting surface can reflect from one of the zones associated therewith to the other of the zones associated therewith encloses a free space not traversed by these rays and the second light concentrating reflecting surface is positioned between the two zones associated with the annular reflecting surface inside the said free space.

2. A photoelectric system for sensing light deflected from its direction of propagation by small particles in a fluid comprising a source of light, a photosensor having a light sensitive surface, two spaced light concentration zones and an inspection zone, means for directing the fluid to the inspection zone, a first of the said light concentration zones receiving light from the source of light, the said inspection zone being created by providing a first light concentrating reflecting surface so designed and arranged that it concentrates light from said first of the light concentration zones into the inspection zone and a second light concentrating reflecting surface so designed and arranged that it concentrates light deflected by particles at the inspection zone from the inspection zone toward a second of the light concentration zones, the said light sensitive surface being so placed that it intercepts light concentrated by the said second light concentrating reflecting surface toward the second of the light concentration zones, one of the said reflecting surfaces being located wholly outside a full cone having its apex at the inspection zone and the other of the said reflecting surfaces being located wholly inside the said full cone, the second light concentrating reflecting surface being of annular shape, whereby the space traversed by rays that the annular reflecting surface can reflect from one of the zones associated therewith to the other of the zones associated therewith encloses a free space not traversed by these rays and the first light concentrating reflecting surface is positioned between the two zones associated with the annular reflecting surface inside the said free space.

3. In a system for sensing light deflected from its direction of propagation by small particles in a fluid comprising means to send the fluid along a predetermined fluid path, a source of illumination, a photosensor having a light sensitive surface, a first optical means so designed and arranged that it can direct illumination from the said source of illumination toward an inspection zone in the said fluid path, the said first optical means comprising a reflecting surface facing the inspection zone so designed and arranged that it concentrates light at the inspection zone, a second optical means so designed and arranged that it can direct light deflected by particles in the inspection zone toward the said light sensitive surface, the said second optical means comprising a second reflecting surface facing the inspection zone so designed and arranged that it can direct toward the said light sensitive surface light deflected by particles in the inspection zone and falling on it, one of the two said reflecting surfaces being located wholly outside a full cone comprising two half cones that may be drawn with its apex at the inspection zone, the other of the two said reflecting surfaces being located wholly inside one of the two said half cones, the said reflecting surface located outside the said full cone having an annular shape, the said reflecting surface located inside the said half cone being saucer shaped, the said two reflecting surfaces having elliptical curvature and being so designed and arranged that each reflecting surface conjugates the inspection zone with one of two light concentration zones, a spherical reflecting surface having its center of curvature at the inspection zone facing the inspection zone in a direction opposite to the direction in which the said saucer shaped reflecting surface faces the inspection zone, a transparent opening in the said spherical reflecting surface forming the light concentration zone with which the said saucer shaped reflecting surface conjugates the inspection zone.

4. In a system for sensing light deflected from its direction of propagation by small particles in a fluid comprising means to send the fluid along a predetermined fluid path, a source of illumination, a photosensor having a light sensitive surface, a first optical means so designed and arranged that it can direct illumination from the said source of illumination toward an inspection zone in the said fluid path, the said first optical means comprising a reflecting surface facing the inspection zone so designed and arranged that it concentrates light at the inspection zone, a second optical means so designed and arranged that it can direct light deflected by particles in the inspection zone toward the said light sensitive surface, the said second optical means comprising a second reflecting surface facing the inspection zone so designed and arranged that it can direct toward the said light sensitive surface light deflected by particles in the inspection zone and falling on it, one of the two said reflecting surfaces being located wholly outside a full cone comprising two half cones that may be drawn with its apex at the inspection zone, the other of the two said reflecting surfaces being located wholly inside one of the two said half cones, the said reflecting surface located outside the said full cone having an annular shape, the said reflecting surface located inside the said half cone being saucer shaped, the said two reflecting surfaces having elliptical curvature and being so designed and arranged that each reflecting surface conjugates the inspection zone with one of two light concentration zones, and a spherical reflecting surface having its center of curvature at the inspection zone facing the inspection zone in a direction opposite to the direction in which the said saucer shaped reflecting surface faces the inspection zone, a transparent opening in the said spherical reflecting surface clearing the path of rays between the said saucer shaped reflecting surface and the light concentration zone with which it conjugates the inspection zone.

5. In a system for sensing light deflected from its direction of propagation by small particles in a fluid comprising means to send the fluid along a predetermined fluid path, a source of illumination, a photosensor having a light sensitive surface, a first optical means so designed and arranged that it can direct illumination from the said source of illumination toward an inspection zone in the said fluid path, the said first optical means comprising a reflecting surface facing the inspection zone so designed and arranged that it concentrates light at the inspection zone, a second optical means so designed and arranged that it can direct light deflected by particles in the inspection zone toward the said light sensitive surface, the said second optical means comprising a second reflecting surface facing the inspection zone so designed and arranged that it can direct toward the said light sensitive surface light deflected by particles in the inspection zone and falling on it, one of the two said reflecting surfaces being located wholly outside a full cone comprising two half cones that may be drawn with its apex at the inspection zone, and the other of the two said reflecting surfaces being located wholly inside one of the two said half cones, the said reflecting surface located outside the said full cone having an annular shape, the said reflecting surface located inside the said half cone being saucer shaped, the said two reflecting surfaces having elliptical curvature and being so designed and arranged that each reflecting surface conjugates the inspection zone with one of two light concentration zones, the two said light concentration zones being located on a straight line traversing the inspection zone, creating thereby a common optical axis for the two reflecting surfaces.

6. A system as in claim 5 in which there is means that cause the fluid to be tested to traverse the said inspection zone in a stream centered around the said optical axis.

7. In a system for sensing light deflected from its direction of propagation by small particles in a fluid comprising means to send the fluid along a predetermined fluid path, a source of illumination, a photosensor having a light sensitive surface, a first optical means so designed and arranged that it can direct illumination from the said source of illumination toward an inspection zone in the said fluid path, the said first optical means comprising a reflecting surface facing the inspection zone so designed and arranged that it concentrates light at the inspection zone, a second optical means so designed and arranged that it can direct light deflected by particles in the inspection zone toward the said light sensitive surface, the said second optical means comprising a second reflecting surface facing the inspection zone so designed and arranged that it can direct toward the said light sensitive surface light deflected by particles in the inspection zone and falling on it, one of the two said reflecting surfaces being located wholly outside a full cone comprising two half cones that may be drawn with its apex at the inspection zone, and the other of the two said reflecting surfaces being located wholly inside one of the two said half cones, at least one of the said reflecting surfaces being a reflecting coating on the outside of a transparent body, in which an interior path is provided for sending the fluid to be tested through the said inspection zone, another part of the outside of the said transparent body being shaped spherically with the center of its curvature at the inspection zone and being covered at least partly with a reflecting coating.

8. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions different from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, the location of the said two reflecting surfaces facing the inspection zone being further limited to one side of a plane traversing the apex of the said full cone, and the system includes a third reflecting surface facing the inspection zone having spherical curvature with its center of curvature at the said inspection zone and facing the inspection zone from the other side of said plane.

9. In a system for sensing light deflected from its direction of propagation by small particles in a fluid comprising means to send the fluid along a predetermined fluid path, a source of illumination, a photosensor having a light sensitive surface, a first optical means so designed and arranged that it can direct illumination from the said source of illumination toward an inspection zone in the said fluid path, the said first optical means comprising a reflecting surface facing the inspection zone so designed and arranged that it concentrates light at the inspection zone, a second optical means so designed and arranged that it can direct light deflected by particles in the inspection zone toward the said light sensitive surface, the said second optical means comprising a second reflecting surface facing the inspection zone so designed and arranged that it can direct toward the said light sensitive surface light deflected by particles in the inspection zone and falling on it, one of the two said reflecting surfaces being located wholly outside a full cone comprising two half cones that may be drawn with its apex at the inspection zone, and the other of the two said reflecting surfaces being located wholly inside one of the two said half cones, the said reflecting surface located outside the said full cone having an annular shape, the said reflecting surface located inside the said half cone being saucer shaped, the location of the said two reflecting surfaces facing the inspection zone being further limited to one side of a plane traversing the apex of the said full cone, the system including a third reflecting surface facing the inspection zone having spherical curvature with its center of curvature at the said inspection zone and facing the inspection zone from the other side of said plane, the said plane traversing the apex of the said cone being located outside the said full cone the said full cone having a centerline, and the said plane being perpendicular to the said centerline.

10. In a system for sensing light deflected from its direction of propagation by small particles in a fluid comprising means to send the fluid along a predetermined fluid path, a source of illumination, a photosensor having a light sensitive surface, a first optical means so designed and arranged that it can direct illumination from the said source of illumination toward an inspection zone in the said fluid path, the said first optical means comprising a first reflecting surface facing the inspection zone so designed and arranged that it concentrates light at the inspection zone, a second optical means so designed and arranged that it can direct light deflected by particles in the inspection zone toward the said light sensitive surface, the said second optical means comprising a second reflecting surface facing the inspection zone so designed and arranged that it can direct toward the said light sensitive surface light deflected by particles in the inspection zone and falling on it, one of the two said reflecting surfaces being located wholly outside a full cone comprising two half cones that may be drawn with its apex at the inspection zone, and the other of the two said reflecting surfaces being located wholly inside one of the two said half cones, the said reflecting surface located wholly outside the said full cone conjugating the inspection zone with a light concentration zone by rays which surround a space not traversed by these rays and the said reflecting surface located inside one of the said two half cones being arranged also inside the said space.

11. In a photoelectric system for sensing light deflected from its direction of propagation by microscopic or sub-microscopic particles in a fluid comprising means for sending the fluid along a predetermined fluid path, a light source, a non-transparent surface having a transparent opening therein between the light source and a zone of the fluid path, a photosensor having a light sensitive surface, a first reflecting surface so designed and arranged that it reflects rays reaching it from the said light source toward the transparent opening in the non-transparent surface, a second light reflecting surface so designed and arranged that it reflects light reaching it from the said transparent opening toward the said zone of the said fluid path, and a third light reflecting surface so designed and arranged that it reflects light reaching it from the said zone of the said fluid path toward the said light sensitive surface, the said third reflecting surface being of annular shape so that rays reflected by it from said zone toward the said light sensitive surface surround a space not traversed by these rays, and the said second reflecting surface being arranged inside this space not traversed by these rays.

12. In a photoelectric system for sensing light deflected from its direction of propagation by microscopic or sub-microscopic particles in a fluid comprising means for sending the fluid along a predetermined fluid path, a light source, a non-transparent surface having a transparent opening therein between the light source and a zone of the fluid path, a photosensor having a light sensitive surface, a first reflecting surface so designed and arranged that it reflects rays reaching it from the said light source toward the transparent opening in the non-transparent surface, a second light reflecting surface so designed and arranged that it reflects light reaching it from the said transparent opening toward the said zone of the said fluid path, and a third light reflecting surface so designed and arranged that it reflects light reaching it from the said zone of the said fluid path toward the said light sensitive surface, the said second reflecting surface being of annular shape so that rays reflected by it from the said transparent opening toward the said zone surround a space not traversed by these rays, and the said third reflecting surface being arranged inside this space not traversed by these rays.

13. In a photoelectric system for sensing light deflected from its direction of propagation by microscopic or sub-microscopic particles in a fluid comprising means for sending the fluid along a predetermined fluid path, a light source, a non-transparent surface having a transparent opening therein between the light source and a zone of the fluid path, a photosensor having a light sensitive surface, a first reflecting surface so designed and arranged that it reflects rays reaching it from the said light source toward the transparent opening in the non-transparent surface, a second light reflecting surface so designed and arranged that it reflects light reaching it from the said transparent opening toward the said zone of the said fluid path, and a third light reflecting surface so designed and arranged that it reflects light reaching it from the said zone of the said fluid path toward the said light sensitive surface, the system including a fourth reflecting surface having spherical curvature with the center of its curvature at the said zone of the fluid path so that it reflects light reaching it from the said zone back toward the said zone, the said second and third reflecting surfaces facing the said zone of the fluid path from one side of a plane through the said zone and the said fourth reflecting surface facing it from the other side of this plane.

14. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, the two said reflecting surfaces having elliptical curvature and being so designed and arranged that both of the said two reflecting surfaces conjugate the inspection zone with one of two light concentration zones, and the system includes a third spherical reflecting surface having its center of curvature at the inspection zone facing the inspection zone in a direction opposite to the direction in which the said saucer shaped reflecting surface faces the inspection zone, and a transparent opening in the said spherical reflecting surface forming the light concentration zone with which the said saucer shaped reflecting surface conjugates the inspection zone.

15. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions different from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, the two said reflecting surfaces having elliptical curvature and being so designed and arranged that both of the said two reflecting surfaces conjugate the inspection zone with one of two light concentration zones, and the system includes a third spherical reflecting surface having its center of curvature at the inspection zone facing the inspection zone in a direction opposite to the direction in which the said saucer shaped reflecting surface faces the inspection zone, and a transparent opening in the said third spherical reflecting surface clearing the path of rays between the said saucer shaped reflecting surface and the light concentration zone with which it conjugates the inspection zone.

16. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions different from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, the two said reflecting surfaces having elliptical curvature and being so designed and arranged that both of the said two reflecting surfaces conjugate the inspection zone with one of two light concentration zones, the two said light concentration zones being located on a straight line traversing the inspection zone, creating thereby a common optical axis for the two reflecting surfaces.

17. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions different from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, at least one of the said reflecting surfaces being a reflecting coating on the outside of a transparent body in which an interior path is provided for sending the fluid to be tested through the said inspection zone, another part of the outside of the said transparent body being shaped spherically with the center of its curvature at the inspection zone and being covered at least partly with a reflecting coating.

18. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions different from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, the two said reflecting surfaces facing the inspection zone only from one side of a plane traversing the apex of the said cone and situated outside of the said cone, and the system includes a third spherical reflecting surface having its center of curvature at the inspection zone facing the inspection zone from the other side of the said plane.

19. In a photoelectric particle sensing system comprising a light source, a photosensor having a light sensitive surface, means to conduct a fluid to be tested on a predetermined path, a first reflecting surface suitable for directing light of the said light source toward an inspection zone which is a selected region of the said path, and a second reflecting surface suitable to direct toward the said light sensitive surface light leaving the said inspection zone in directions different from the directions in which the said first reflecting surface directs light toward the inspection zone, the improvement that one of the said two reflecting surfaces is of annular shape and faces the inspection zone from the outside of a full cone consisting of two half cones and having its apex at the said inspection zone, so that this reflecting surface can face the inspection zone from essentially all directions outside the said full cone, and the other of the said two reflecting surfaces is saucer shaped and faces the inspection zone from the inside of one of the said half cones, so that this other of the said two reflecting surfaces can face the inspection zone from essentially all directions inside the said half cone, the said annular reflecting surface conjugating the inspection zone with a light concentration zone by rays which surround a space not traversed by these rays, the said saucer shaped reflecting surface being arranged inside the said space.

* * * * *